(12) United States Patent
Gaspar et al.

(10) Patent No.: US 10,100,002 B2
(45) Date of Patent: Oct. 16, 2018

(54) METHOD FOR SEPARATING N,N,N'-TRIMETHYLBISAMINOETHYLETHER AND/OR N,N-DIMETHYLBISAMINOETHYLETHER FROM A MIXTURE

(71) Applicants: Huntsman International LLC, The Woodlands, TX (US); Huntsman Corporation Hungary ZRT, Gyartelep (HU)

(72) Inventors: Attila Gaspar, Petfurdo (HU); Zsolt Gaspar, Petfurdo (HU); Zsanett Szabone Herseczki, Varpalota (HU); Heiko Heinrich Humbert, Hamburg (DE); Imre Kordas, Veszprem (HU); Petra Emma Vanderstraeten, Leuven (BE)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 0 days.

(21) Appl. No.: 15/029,647

(22) PCT Filed: Sep. 29, 2014

(86) PCT No.: PCT/EP2014/070722
§ 371 (c)(1),
(2) Date: Apr. 15, 2016

(87) PCT Pub. No.: WO2015/055406
PCT Pub. Date: Apr. 23, 2015

(65) Prior Publication Data
US 2016/0237024 A1  Aug. 18, 2016

(30) Foreign Application Priority Data
Oct. 15, 2013  (EP) .................................... 13462004

(51) Int. Cl.
| | | |
|---|---|---|
| C07C 209/00 | (2006.01) | |
| C07C 213/08 | (2006.01) | |
| B01D 3/36 | (2006.01) | |
| C07C 213/10 | (2006.01) | |
| C07C 213/02 | (2006.01) | |

(52) U.S. Cl.
CPC .............. *C07C 213/08* (2013.01); *B01D 3/36* (2013.01); *C07C 213/02* (2013.01); *C07C 213/10* (2013.01)

(58) Field of Classification Search
CPC ..................................................... C07C 217/08
See application file for complete search history.

(56) References Cited

U.S. PATENT DOCUMENTS

| | | |
|---|---|---|
| 5,874,483 A | 2/1999 | Coates Lescher |
| 7,009,081 B2 | 3/2006 | Mitchell |
| 8,232,223 B2 | 7/2012 | Kordas et al. |
| 2012/0130132 A1 | 5/2012 | Humbert et al. |

FOREIGN PATENT DOCUMENTS

| | | |
|---|---|---|
| CN | 101678342 A | 3/2010 |
| JP | H09124761 A | 5/1997 |
| JP | 2005053913 A | 3/2005 |
| JP | 2010526815 A | 8/2010 |
| WO | 2008/140957 A | 11/2008 |
| WO | 2010/139520 A | 12/2010 |
| WO | 2010139521 A | 12/2010 |

*Primary Examiner* — Ana Z Muresan
(74) *Attorney, Agent, or Firm* — Huntsman International LLC; Lewis D. Craft

(57) ABSTRACT

The present invention relates to a method for separating N,N,N'-trimethylbisaminoethylether and/or N,N-dimethylbisaminoethylether, from a mixture A comprising N,N,N'-trimethylbisaminoethylether, and N,N-dimethylbisaminoethylether, wherein said method comprises the steps of:
(a) contacting said mixture A with an acylating agent, to form a mixture B comprising the amides of N,N,N'-trimethylbisaminoethylether and of N,N-dimethylbisaminoethylether, respectively; and
(b1) separating the amide of N,N,N'-trimethylbisaminoethylether from mixture B; and (c1) recovering N,N,N'-trimethylbisaminoethylether from its amide by means of a transamidation reaction;
and/or
(b2) separating the amide of N,N-dimethylbisaminoethylether from mixture B; and (c2) recovering N,N-dimethylbisaminoethylether from its amide by means of a transamidation reaction.

13 Claims, No Drawings

METHOD FOR SEPARATING N,N,N'-TRIMETHYLBISAMINOETHYLETHER AND/OR N,N-DIMETHYLBISAMINOETHYLETHER FROM A MIXTURE

CROSS-REFERENCE TO RELATED APPLICATIONS

This application is the National Phase of International Application PCT/EP2014/070722 filed Sep. 29, 2014 which designated the U.S. and which claims priority to E.P. Application Serial No. 13462004.6 filed Oct. 15, 2013. The noted applications are incorporated herein by reference.

FIELD OF THE INVENTION

The present invention relates to separation or recovering of N,N,N'-trimethylbisaminoethylether. The present invention also relates to separation or recovering of N,N-dimethylbisaminoethylether.

BACKGROUND TO THE INVENTION

Compounds such as alkylbisaminoalkylethers are often used as polyurethane catalyst or as precursors for the provision of polyurethane catalysts. N,N,N'-trimethylbisaminoethylether (T3MBAEE) is for example an important chemical compound and can be used as a precursor for the manufacturing of catalysts.

In general, blends or mixtures of primary, secondary and tertiary amines are often obtained in industrial processes aimed at providing just one of the above mentioned alkylbisaminoalkylethers. In particular, mixtures of primary amines such as N,N-dimethylbisaminoethylether (T2MBAEE); and secondary amines such as N,N,N'-trimethylbisaminoethylether (T3MBAEE); and tertiary amine such as N,N,N',N'-tetramethylbisaminoethylether (T4MBAEE), may be obtained. These amines have boiling points fairly close to each other. Thus, any distillative purification of such mixture is extremely difficult.

At present, there is no economically acceptable production process for providing high quantity and high purity N,N,N'-trimethylbisaminoethylether.

SUMMARY OF THE INVENTION

It is an object of the present invention to provide a method for separating or recovering N,N,N'-trimethylbisaminoethylether from a mixture further comprising N,N,N'-trimethylbisaminoethylether and N,N-dimethylbisaminoethylether, and optionally one or more compounds selected from N,N,N',N'-tetramethylbisaminoethylether, N,N'-dimethylbisaminoethylether, and N-monomethylbisaminoethylether; which method provides the secondary amine N,N,N'-trimethylbisaminoethylether in substantially pure form and in an industrially acceptable yield.

The present inventors have found a way to separate or recover N,N,N'-trimethylbisaminoethylether, independently of each component's starting concentrations, overcoming the above and other problems of the prior art. The present inventors have also found a way to separate or recover N,N-dimethylbisaminoethylether, independently of each component's starting concentrations. The present methods may lead to lower production costs, better controlled process conditions and more optimal end-products.

According to a first aspect of the present invention, a method for separating N,N,N'-trimethylbisaminoethylether and/or N,N-dimethylbisaminoethylether, from a mixture A comprising N,N,N'-trimethylbisaminoethylether, N,N-dimethylbisaminoethylether, and N,N,N',N'-tetramethylbisaminoethylether, is provided. Said method comprises the steps of:
(a) contacting said mixture A with an acylating agent, to form a mixture B comprising N,N,N',N'-tetramethylbisaminoethylether, the amides of N,N,N'-trimethylbisaminoethylether and of N,N-dimethylbisaminoethylether, respectively;
(b1) separating the amide of N,N,N'-trimethylbisaminoethylether from mixture B; and/or
(b2) separating the amide of N,N-dimethylbisaminoethylether from mixture B;
(c1) recovering N,N,N'-trimethylbisaminoethylether from its amide by means of a transamidation reaction and/or
(c2) recovering N,N-dimethylbisaminoethylether from its amide by means of transamidation reaction.

According to a second aspect of the present invention, a method for separating N,N'-dimethylbisaminoethylether from a mixture A comprising N,N,N'-trimethylbisaminoethylether, N,N'-dimethylbisaminoethylether, and N,N-dimethylbisaminoethylether, and optionally N,N,N',N'-tetramethylbisaminoethylether, and optionally N-monomethylbisaminoethylether is provided. Said method comprises the steps of:
contacting said mixture A with an acylating agent, to form a mixture B comprising the amides of N,N,N'-trimethylbisaminoethylether, and N,N-dimethylbisaminoethylether and N,N'-dimethylbisaminoethylether, respectively;
separating the amide of N,N'-dimethylbisaminoethylether from said mixture B; and
recovering N,N'-dimethylbisaminoethylether from its amide by means of a transamidation reaction.

According to a third aspect of the present invention, a method for preparing N,N-dimethylbisaminoethylether is provided, said method comprising the step of contacting 2-(2-dimethylaminoethoxy)-ethanol with monomethylamine, preferably in the presence of a catalyst.

According to a further aspect of the present invention, a method for separating N,N-dimethylbisaminoethylether from a mixture comprising N,N-dimethylbisaminoethylether and other amines is also provided. Said method according to the further aspect comprises the steps of:
1) contacting said mixture with an acylating agent, to form a mixture comprising the amides of N,N-dimethylbisaminoethylether and of the other amines, respectively;
2) separating the amide of N,N-dimethylbisaminoethylether from the mixture obtained in step 1; and
3) recovering N,N-dimethylbisaminoethylether from its amide by means of a transamidation reaction.

The present invention further encompasses a compound selected from the group comprising N,N-dimethylbisaminoethylether-formamide and N,N'-dimethylbisaminoethylether-bisformamide, and N-monomethylbisaminoethylether-bisformamide.

Surprisingly, the present inventors have found that the invention leads to lower production costs, better controlled process conditions and more optimal end-products. The present inventors have found that the invention provides a method that readily allows the separation of N,N,N'-trimethylbisaminoethylether (T3MBAEE), from a complex amine mixture comprising N,N,N'-trimethylbisaminoethylether, N,N-dimethylbisaminoethylether (T2MBAEE), and optionally N,N,N',N'-tetramethylbisaminoethylether (T4MBAEE), optionally N,N'-dimethylbisaminoethylether (T2MAEE), and optionally N-monomethylbisaminoethylether (T1MAEE). In particular, the present inventors have surprisingly found that the formamide derived from N,N,N'-trimethylbisaminoethylether, boils at much lower temperature than the amides derived from T2MBAEE, T2MAEE and T1MAEE, allowing the separation by a simple fractionated distillation of N,N,N'-trimethylbisaminoethylether formamide, at a purity of at least 90%, for example at least 95%, for example of at least 99% by weight. Furthermore, the present inventors have also surprisingly found that the formamide derived from N,N-dimethylbisaminoethylether, boils at much lower temperature than the amides derived from T2MAEE** and T1MAEE, allowing the separation by distillation of T2MAEE-formamide, at a purity of at least 90%, for example at least 95%, for example of at least 98% by weight.

Moreover, the present inventors have also surprisingly isolated the bisformamide derived from N,N'-dimethylbisaminoethylether (T2MAEE**-bisformamide), as a bottom product, at a purity of at least 90%, for example at least 92%, for example of at least 93% by weight.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Before the present method used in the invention is described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

When reference is made to boiling points or boiling temperature, unless otherwise indicated, the boiling temperature indicates the boiling point or boiling temperature under atmospheric pressure.

Unless otherwise indicated, any percentage of a component refers to weight percentages over the total weight of the substance in which the individual component is present.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the following, N,N,N'-trimethylbisaminoethylether may be abbreviated by T3MBAEE or T3. Throughout the text, the notations of T3MBAEE, T3 and N,N,N'-trimethylbisaminoethylether may be used interchangeably.

In the following, N,N,N',N'-tetramethylbisaminoethylether may be abbreviated by T4MBAEE or T4. Throughout the text, the notations of T4MBAEE, T4 and N,N,N',N'-tetramethylbisaminoethylether may be used interchangeably.

In the following, N,N-dimethylbisaminoethylether may be abbreviated by T2MBAEE or T2. Throughout the text, the notations of T2MBAEE, T2 and N,N-dimethylbisaminoethylether may be used interchangeably.

In the following, N,N'-dimethylbisaminoethylether may be abbreviated by T2MBAEE or T2. Throughout the text, the notations of T2MBAEE, T2 and N,N'-dimethylbisaminoethylether may be used interchangeably.

In the following, N-monomethylbisaminoethylether may be abbreviated with T1MBAEE or T1. Throughout the text, the notations of T1MBAEE, T1 and N-monomethylbisaminoethylether may be used interchangeably.

A first aspect of the present invention relates to a method for separating N,N,N'-trimethylbisaminoethylether from a mixture A comprising N,N,N'-trimethylbisaminoethylether, N,N-dimethylbisaminoethylether, and N,N,N',N'-tetramethylbisaminoethylether said method comprising the steps of:

(a') providing a mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether and the amides of N,N,N'-trimethylbisaminoethylether, and of N,N-dimethylbisaminoethylether, respectively;
(b1) separating the amide of N,N,N'-trimethylbisaminoethylether from mixture B; and
(c1) recovering N,N,N'-trimethylbisaminoethylether from its amide by means of a transamidation reaction.

Preferably, the method also comprises the step (i) of separating N,N,N',N'-tetramethylbisaminoethylether from mixture B; preferably wherein said separation step (i) is performed prior to step (b1).

In some preferred embodiment, the method comprises the steps of:
(a') providing a mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether, and the amides of N,N,N'-trimethylbisaminoethylether, and N,N-dimethylbisaminoethylether, respectively;
(i) prior to step (b1), separating N,N,N',N'-tetramethylbisaminoethylether from mixture B;
(b1) separating the amide of N,N,N'-trimethylbisaminoethylether from mixture B; and
(c1) recovering N,N,N'-trimethylbisaminoethylether from its amide by means of a transamidation reaction.

In an embodiment, the method also comprises the further step of: (b2) separating the amide of N,N-dimethylbisaminoethylether from mixture B. Preferably, step (b2) is performed after step (b1).

In some preferred embodiments, the method can comprise the steps of:
(a') providing mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether, the amides of N,N,N'-trimethylbisaminoethylether, and of N,N-dimethylbisaminoethylether, respectively;
(b1) separating the amide of N,N,N'-trimethylbisaminoethylether from mixture B; and/or
(b2) subsequently separating the amide of N,N-dimethylbisaminoethylether from mixture B; and
(c1) recovering N,N,N'-trimethylbisaminoethylether from its amide by means of a transamidation reaction.

In some embodiments, the method can comprise the steps of:
(a') providing mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether the amides of N,N,N'-trimethylbisaminoethylether, and of N,N-dimethylbisaminoethylether, respectively;
(b1) separating the amide of N,N,N'-trimethylbisaminoethylether from mixture B; and/or
(b2) subsequently separating the amide of N,N-dimethylbisaminoethylether from mixture B;
(c1) recovering N,N,N'-trimethylbisaminoethylether from its amide by means of a transamidation reaction; and/or
(c2) recovering N,N-dimethylbisaminoethylether from its amide by means of a transamidation reaction.

In some preferred embodiments, the method comprises the steps of:
(a') providing a mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether, and the amides of N,N,N'-trimethylbisaminoethylether, and N,N-dimethylbisaminoethylether, respectively;
(i) prior to step (b1) or (b2), separating N,N,N',N'-tetramethylbisaminoethylether from mixture B;
(b1) subsequently separating the amide of N,N,N'-trimethylbisaminoethylether from mixture B; and/or
(b2) subsequently separating the amide of N,N-dimethylbisaminoethylether from mixture B; and
(c1) recovering N,N,N'-trimethylbisaminoethylether from its amide by means of a transamidation reaction. In some embodiments, the method can comprise the steps of:
(a') providing a mixture A comprising N,N,N'-trimethyl-bisaminoethylether, N,N,N',N'-tetramethylbisaminoethylether, and N,N-dimethylbisaminoethylether,
(a) contacting said mixture A with an acylating agent, to form a mixture B comprising N,N,N',N'-tetramethylbisaminoethylether, and the amides of N,N,N'-trimethylbisaminoethylether, and N,N-dimethylbisaminoethylether, respectively;
(i) prior to step (b1), separating N,N,N',N'-tetramethylbisaminoethylether from mixture B;
(b1) separating the amide of N,N,N'-trimethylbisaminoethylether from mixture B; and/or
(b2) subsequently separating the amide of N,N-dimethylbisaminoethylether from mixture B;
(c1) recovering N,N,N'-trimethylbisaminoethylether from its amide by means of a transamidation reaction; and
(c2) recovering N,N-dimethylbisaminoethylether from its amide by means of a transamidation reaction.

In some embodiments, said mixture A further comprises N,N'-dimethylbisaminoethylether, and said mixture B comprises the amide of N,N'-dimethylbisaminoethylether.

In some embodiments, the method comprises the steps of
(a') providing a mixture A comprising N,N,N'-trimethyl-bisaminoethylether, N,N,N',N'-tetramethylbisaminoethylether, N,N-dimethylbisaminoethylether, and N,N'-dimethylbisaminoethylether,
(a) contacting said mixture A with an acylating agent, to form a mixture B comprising N,N,N',N'-tetramethylbisaminoethylether, and the amides of N,N,N'-trimethylbisaminoethylether, of N,N-dimethylbisaminoethylether, and of N,N'-dimethylbisaminoethylether, respectively;
(b1) separating the amide of N,N,N'-trimethylbisaminoethylether from mixture B; and
(c1) recovering N,N,N'-trimethylbisaminoethylether from its amide by means of a transamidation reaction.

In some embodiment, the present method further comprises the step (b3) of separating the amide of N,N'-dimethylbisaminoethylether from mixture B; preferably wherein said separation step (b3) is performed after step (b1).

In some embodiments, the method comprises the steps of
(a') providing a mixture A comprising N,N,N'-trimethyl-bisaminoethylether, N,N,N',N'-tetramethylbisaminoethylether, N,N-dimethylbisaminoethylether, and N,N'-dimethylbisaminoethylether, (a) contacting said mixture A with an acylating agent, to form a mixture B comprising N,N,N',N'-tetramethylbisaminoethylether, and the amides of N,N,N'-trimethylbisaminoethylether, of N,N-dimethylbisaminoethylether, and of N,N'-dimethylbisaminoethylether, respectively;

(i) prior to step (b1), separating N,N,N',N'-tetramethylbisaminoethylether from mixture B;

(b1) separating the amide of N,N,N'-trimethylbisaminoethylether from mixture B; and/or (b2) subsequently separating the amide of N,N-dimethylbisaminoethylether from mixture B; and/or (b3) optionally subsequently isolating the amide of N,N'-dimethylbisaminoethylether from mixture B; and (c1) recovering N,N,N'-trimethylbisaminoethylether from its amide by means of a transamidation reaction.

In an embodiment of the present invention, mixture A also comprises N-monomethylbisaminoethylether, preferably at least 0.001% by weight of N-monomethylbisaminoethylether, based on the total weight of mixture A, for example at least 0.01%, for example at least 0.1% by weight.

In some embodiments, the method comprises the steps of (a') providing a mixture A comprising N,N,N'-trimethylbisaminoethylether, N,N,N',N'-tetramethylbisaminoethylether, N,N-dimethylbisaminoethylether, optionally N,N'-dimethylbisaminoethylether, and optionally N-monomethylbisaminoethylether, (a) contacting said mixture A with an acylating agent, to form a mixture B comprising N,N,N',N'-tetramethylbisaminoethylether, and the amides of N,N,N'-trimethylbisaminoethylether, of N,N-dimethylbisaminoethylether, optionally the amide of N,N'-dimethylbisaminoethylether, respectively and optionally the amide of N-monomethylbisaminoethylether;

(i) prior to step (b1), separating N,N,N',N'-tetramethylbisaminoethylether from mixture B;

(b1) separating the amide of N,N,N'-trimethylbisaminoethylether from mixture B; and/or (b2) optionally subsequently separating the amide of N,N-dimethylbisaminoethylether from mixture B; and/or (b3) optionally subsequently isolating the amide of N,N'-dimethylbisaminoethylether from mixture B; and (c1) recovering N,N,N'-trimethylbisaminoethylether from its amide by means of a transamidation reaction, and/or (c2) recovering N,N-dimethylbisaminoethylether from its amide by means of a transamidation reaction; and/or (c3) recovering N,N'-dimethylbisaminoethylether from its amide by means of a transamidation reaction.

The first step of the method comprises providing a mixture A comprising N,N,N'-trimethylbisaminoethylether, N,N-dimethylbisaminoethylether, N,N,N',N'-tetramethylbisaminoethylether, optionally N,N'-dimethylbisaminoethylether, and optionally N-monomethylbisaminoethylether. For example, said mixture A comprises N,N,N'-trimethylbisaminoethylether, N,N-dimethylbisaminoethylether, N,N,N',N'-tetramethylbisaminoethylether, N,N'-dimethylbisaminoethylether, and optionally N-monomethylbisaminoethylether.

According to a preferred embodiment, mixture A can be prepared by contacting 2-(2-dimethylaminoethoxy)-ethanol with monomethylamine; preferably in the presence of a catalyst. Mixture A can also be prepared by contacting 2-(2-dimethylaminoethoxy)-ethanol with ammonia, preferably in the presence of a catalyst.

Non limiting examples of suitable catalysts include copper containing catalysts. Suitable catalysts can be selected from the group comprising copper chromite catalyst such as CuO/$Cr_2O_3$ catalyst, $2CuOxCr_2O_3$ (CAS#99328-50-4), $Cr_5CuO_5$ and the like; and Cu/ZnO/$Al_2O_3$ catalyst, and the like.

In some preferred embodiments, the method comprises the steps of (a'') preparing mixture A using a process comprising the step of contacting 2-(2-dimethylaminoethoxy)-ethanol with monomethylamine; preferably in the presence of a catalyst, preferably a copper chromite catalyst; thereby obtaining mixture A comprising N,N,N'-trimethylbisaminoethylether, N,N,N',N'-tetramethylbisaminoethylether, N,N-dimethylbisaminoethylether, optionally N,N'-dimethylbisaminoethylether, and optionally N-monomethylbisaminoethylether;

(a) contacting said mixture A with an acylating agent, to form a mixture B comprising N,N,N',N'-tetramethylbisaminoethylether, and the amides of N,N,N'-trimethylbisaminoethylether and of N,N-dimethylbisaminoethylether, respectively, optionally the amide of N,N'-dimethylbisaminoethylether, and optionally the amide of N-monomethylbisaminoethylether;

(i) prior to step (b1), separating N,N,N',N'-tetramethylbisaminoethylether from mixture B;

(b1) separating the amide of N,N,N'-trimethylbisaminoethylether from mixture B; and/or (b2) optionally subsequently separating the amide of N,N-dimethylbisaminoethylether from mixture B; and/or (b3) optionally subsequently separating the amide of N,N'-dimethylbisaminoethylether from mixture B; and (c1) recovering N,N,N'-trimethylbisaminoethylether from its amide by means of a transamidation reaction, and/or (c2) recovering N,N-dimethylbisaminoethylether from its amide by means of a transamidation reaction; and/or (c3) recovering N,N'-dimethylbisaminoethylether from its amide by means of a transamidation reaction.

The step of contacting 2-(2-dimethylaminoethoxy)-ethanol with monomethylamine is preferably performed under pressure, for example at a pressure of at least 5 bar, for example at least 6 bar, for example at least 7 bar, for example at least 8 bar, for example at least 9 bar, for example at least 10 bar.

The next step (a) in the method, comprises contacting mixture A with an acylating agent. The acylation reaction leads to a mixture B comprising the amides of T3MBAEE, T2MBAEE respectively, optionally T4MBAEE, optionally the amide of T2MBAEE**, and optionally the amide of T1MBAEE.

In some embodiments, mixture B can comprise N,N,N'-trimethylbisaminoethylether monoamide, N,N-dimethylbisaminoethylether monoamide, N,N,N',N'-tetramethylbisaminoethylether, optionally N,N'-dimethylbisaminoethylether bisamide, and optionally N-monomethylbisaminoethylether bisamide. For example, said mixture B comprises N,N,N'-trimethylbisaminoethylether monoamide, N,N-dimethylbisaminoethylether monoamide, N,N,N',N'-tetramethylbisaminoethylether, N,N'-dimethylbisaminoethylether bisamide, and optionally N-monomethylbisaminoethylether bisamide.

The acylation step (a) can be carried out by any technique known to the person skilled in the art. The acylation step (a) can be performed by mixing mixture A with at least one acylating agent. Preferably, acylation of the mixture A is carried out with an acylating agent selected from the group comprising a carboxylic acid and a carboxylic acid derivative. In some embodiments, said carboxylic acid and/or carboxylic acid derivative can be selected from the group consisting of acylhalide, anhydride, carboxylic ester and carboxylic amides. Examples of suitable carboxylic acid derivatives are acetylhalides such as acetylchloride and acetylbromide, formic acid anhydride, acetic acid anhydride, formic acid ester, acetic acid ester, formamide and acetamide.

According to a preferred embodiment, the acylation step (a) can be performed with a low molecular weight carboxylic acid as acylating agent, preferably a $C_{1-6}$-carboxylic acid, more preferably formic acid or acetic acid, even more preferably formic acid.

In some preferred embodiments, mixture B comprises N,N,N'-trimethylbisaminoethylether formamide, N,N-dimethylbisaminoethylether formamide, N,N,N',N'-tetramethylbisaminoethylether, optionally N,N'-dimethylbisaminoethylether bisformamide, and optionally N-monomethylbisaminoethylether bisformamide. For example, said mixture B comprises N,N,N'-trimethylbisaminoethylether formamide, N,N-dimethylbisaminoethylether formamide, N,N,N',N'-tetramethylbisaminoethylether, N,N'-dimethylbisaminoethylether bisformamide, and optionally N-monomethylbisaminoethylether bisformamide.

In some preferred embodiments, the method comprises the steps of (a') providing a mixture A comprising N,N,N'-trimethylbisaminoethylether, N,N,N',N'-tetramethylbisaminoethylether, N,N-dimethylbisaminoethylether, optionally N,N'-dimethylbisaminoethylether, and optionally N-monomethylbisaminoethylether;

(a) contacting said mixture A with formic acid, to form a mixture B comprising N,N,N',N'-tetramethylbisaminoethylether, and N,N,N'-trimethylbisaminoethylether formamide, N,N-dimethylbisaminoethylether formamide, optionally N,N'-dimethylbisaminoethylether bisformamide, and optionally N-monomethylbisaminoethylether bisformamide;

(i) prior to step (b1), separating N,N,N',N'-tetramethylbisaminoethylether from mixture B;

(b1) separating the N,N,N'-trimethylbisaminoethylether formamide from mixture B; and (b2) optionally subsequently separating the N,N-dimethylbisaminoethylether formamide from mixture B;

(b3) optionally subsequently separating N,N'-dimethylbisaminoethylether bisformamide from mixture B; and (c1) recovering N,N,N'-trimethylbisaminoethylether from its amide by means of a transamidation reaction, (c2) optionally recovering N,N-dimethylbisaminoethylether from its amide by means of a transamidation reaction;

(c3) optionally recovering N,N'-dimethylbisaminoethylether from its amide by means of a transamidation reaction.

In some preferred embodiments, the method comprises the steps of (a") preparing mixture A using a process comprising the step of contacting 2-(2-dimethylaminoethoxy)-ethanol with monomethylamine; preferably in the presence of a catalyst, preferably a copper chromite catalyst; thereby obtaining mixture A comprising N,N,N'-trimethylbisaminoethylether, N,N,N',N'-tetramethylbisaminoethylether, N,N-dimethylbisaminoethylether, optionally N,N'-dimethylbisaminoethylether, and optionally N-monomethylbisaminoethylether;

(a) contacting said mixture A with formic acid, to form a mixture B comprising N,N,N',N'-tetramethylbisaminoethylether, and N,N,N'-trimethylbisaminoethylether formamide, N,N-dimethylbisaminoethylether formamide, optionally N,N'-dimethylbisaminoethylether bisformamide, and optionally N-monomethylbisaminoethylether bisformamide;

(i) prior to step (b1), separating N,N,N',N'-tetramethylbisaminoethylether from mixture B;

(b1) separating N,N,N'-trimethylbisaminoethylether formamide from mixture B; and/or (b2) separating N,N-dimethylbisaminoethylether formamide from mixture B; and/or (b3) subsequently separating N,N'-dimethylbisaminoethylether bisformamide from mixture B; and (c1) recovering N,N,N'-trimethylbisaminoethylether from its amide by means of a transamidation reaction, and/or (c2) recovering N,N-dimethylbisaminoethylether from its amide by means of a transamidation reaction; and/or (c3) recovering N,N'-dimethylbisaminoethylether from its amide by means of a transamidation reaction.

Particularly, the formation of N,N,N'-trimethylbisaminoethylether formamide, and N,N-dimethylbisaminoethylether formamide, optionally N,N'-dimethylbisaminoethylether bisformamide and optionally N-monomethylbisaminoethylether bisformamide, is preferred.

While tertiary amines such as N,N,N',N'-tetramethylbisaminoethylether are not able to react in the acylation step (a), primary and secondary amines, such as T3MBAEE, and T2MBAEE, optionally T2MBAEE, and optionally T1MBAEE which can be present in mixture A, will form their corresponding mono- and/or di-amides. Accordingly, when mixture A comprising T3MBAEE, T2MBAEE, T4MBAEE, optionally T2MBAEE, and optionally T1MBAEE, is subjected to acylation in the presence of formic acid, unreacted T4MBAEE may be obtained, along with some or all of the formamides shown in Scheme 1.

Scheme 1: potential formamides by formylation of mixture A.

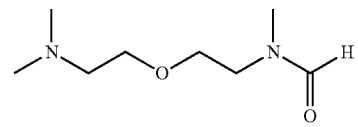

"T3-formamide"

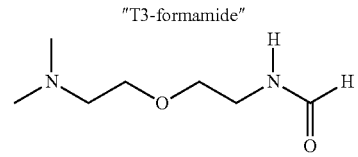

T2-formamide

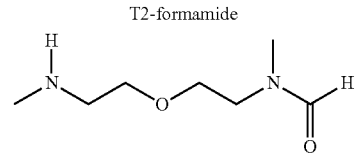

T2**-formamide 1

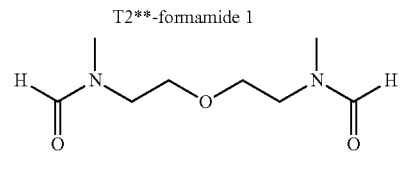

T2**-formamide 2

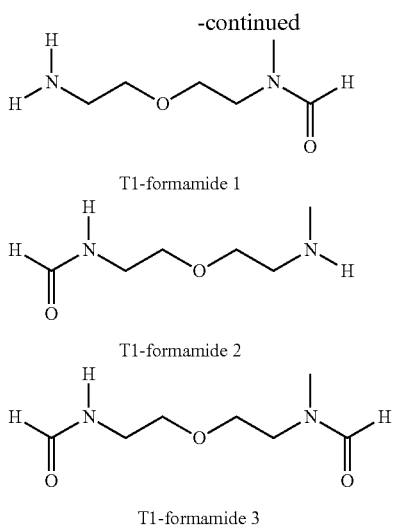

T1-formamide 1

T1-formamide 2

T1-formamide 3

The step of contacting mixture A with carboxylic acids can be performed at a temperature of at least 50° C., for example at least 80° C. In some embodiments, said step (a) is preferably carried out at a temperature ranging from 50 to 250° C. Preferably step (a) is performed under reflux conditions. Preferably step (a) is performed in the presence of a suitable hydrocarbon solvent. The step of contacting mixture A with carboxylic acids can be performed at atmospheric pressure (100 kPa).

The step of contacting mixture A with carboxylic acids can lead to the formation of the amides (such as shown in Scheme 1) as well as water.

In some embodiments, step (a) comprises removing water from the mixture, preferably step (a) comprises continuously removing water from the mixture. In a preferred embodiment of the present invention, step (a) is carried out at a temperature at which water can be removed continuously from the reaction mixture.

The technique to continuously remove water which is obtained during a reaction is known by the person skilled in the art. The water removal process in step (a) is preferably an azeotropic distillation, for example using suitable hydrocarbon solvents.

Hydrocarbons solvents which can be used in step (a) can be saturated, unsaturated and/or aromatic hydrocarbons. In general $C_{6-12}$ aromatic, aliphatic or olefin hydrocarbons are preferred. Particularly, hydrocarbon solvents selected from the group comprising: methylcyclohexane, xylene and blends thereof; hexane, structural isomers and blend thereof; hexene, structural isomers and blends thereof; heptane, structural isomers and blend thereof; heptenes, structural isomers and blend thereof; octane, structural isomers and blend thereof; octenes, structural isomers and blend thereof; cyclohexane; cyclohexene; benzene; methylcyclohexenes, structural isomers and blend thereof; toluene; dimethylcyclohexanes, structural isomers and blend thereof; dimethylcyclohexenes, structural isomers and blend thereof; ethylbenzene, nonenes and nonane hydrocarbons, structural isomers and blend thereof. In some embodiments, said one or more hydrocarbon solvents is selected from the group comprising: methylcyclohexane, xylene, n-hexane, n-hexenes, n-heptane, n-heptenes, n-octane, n-octenes, cyclohexane, cyclohexene, benzene, methylcyclohexenes, dimethylcyclohexanes, dimethylcyclohexenes, ethylbenzene, nonane, nonenes, and toluene. Preferred are hydrocarbons selected from the group comprising methylcyclohexane, toluene, or xylene. Most preferred are hydrocarbons selected from methylcyclohexane, or xylene.

In a preferred embodiment, the amines in mixture B which have not been acylated can be separated from the amides obtained in acylation step (a). For example, the method can comprise the step (i) of separating N,N,N',N'-tetramethylbisaminoethylether from mixture B, preferably by distillation. Preferably, step (i) is performed prior to step (b1). For example, step (i) may be performed after step (a) and prior to step (b1).

In an embodiment, step (i) is carried out by distillation, for example at a temperature of at least 20° C., preferably at a temperature ranging from 20° C. to 250° C. In an embodiment, step (i) is carried out at a pressure of at least 1 mbar, preferably at a pressure ranging from 1 mbar to 1 bar.

Preferably, in step (i), the distillation step can be performed at a temperature ranging from 20° C. to 160° C. The pressure may be chosen in the range of 4 mbar to 150 mbar.

During step (i) N,N,N',N'-tetramethylbisaminoethylether can be removed by distillation from mixture B and due to higher boiling point the amides remain in the distillation residue. Subsequently, the remaining amides can be further distilled.

The next step in the method comprises the step of (b1) separating the amide of N,N,N'-trimethylbisaminoethylether from mixture B. Preferably, said step (b1) is performed after step (i).

Separation step (b1) can in principle be carried out by any known separation technique.

In an embodiment, step (b1) is carried out by distillation. In an embodiment, step (b1) is carried out at a head temperature of at least 50° C., preferably from 50° C. to 250° C. Preferably, in step (b1), the head temperature for the distillation step can range from 120° C. to 210° C., for example from 120° C. to 170° C. In an embodiment, step (b1) is carried out at a pressure ranging from 1 mbar to 1 bar. In some embodiment, the pressure during the distillation may be ranging from 1 mbar to 20 mbar. In an embodiment, step (b1) is performed at a head temperature ranging from 120° C. to 130° C., at a pressure ranging from 1 mbar to 10 mbar, preferably at a head temperature ranging from 120° C. to 125° C. at a pressure ranging from 1 mbar to 5 mbar. In a preferred embodiment, step (b1) is performed at a head temperature ranging from 120° C. to 130° C., at a pressure of 4 mbar, preferably at a head temperature ranging from 120° C. to 125° C. at a pressure of 4 mbar.

In an embodiment, the method comprises the further step of: (b2) separating the amide of N,N-dimethylbisaminoethylether (T2MBAEE-monoamide) from mixture B.

Preferably step (b2) is performed after step (b1). In an embodiment, step (b2) is carried out by distillation. Step (b2) can be carried out at a head temperature of at least 20° C., preferably at a head temperature ranging from 20° C. to 250° C. Preferably, in step (b2), the head temperature for the distillation step can range from 135° C. to 220° C. In an embodiment, step (b2) is carried out at a pressure ranging from 1 mbar to 1 bar. In some embodiment, the pressure during the distillation may be ranging from 1 to 20 mbar. In an embodiment, step (b2) is performed at a head temperature ranging from 135° C. to 140° C., at a pressure ranging from 1 mbar to 10 mbar, preferably at a head temperature ranging from 135° C. to 139° C. at a pressure ranging from 1 mbar to 5 mbar. In a preferred embodiment, step (b2) is performed at a head temperature ranging from 135° C. to 140° C., at a pressure of 4 mbar, preferably at a head temperature ranging from 135° C. to 139° C. at a pressure of 4 mbar.

In an embodiment, mixture A comprises also N,N'-dimethylbisaminoethylether, mixture B comprises N,N'-dimethylbisaminoethylether bisamide, and the method comprises the further step of: (b3) isolating N,N'-dimethylbisaminoethylether bisamide (T2MBAEE** bisamide) from mixture B.

Preferably step (b3) of the isolation of N,N'-dimethylbisaminoethylether bisamide is performed after step (b2). In an embodiment, step (b3) is carried out by distillation. Step (b3) can be carried out at a pot temperature of at least 20° C., preferably at a pot temperature ranging from 20° C. to 250° C. Preferably, in step (b3), the temperature for the distillation step can range from 150° C. to 220° C. In an embodiment, step (b3) is carried out at a pressure ranging from 1 mbar to 1 bar. In some embodiments, the pressure during the distillation may be ranging from 1 to 20 mbar. In some embodiments, step (b3) is performed at a temperature ranging from 198° C. to 207° C., and at a pressure ranging from 2 to 4 mbar.

The present inventors have found that amidated T3MBAEE can be separated from a mixture B further comprising T4MBAEE, amidated T2MBAEE, optionally amidated T2MBAEE and optionally amidated T1MBAEE, by distillation of T4MBAEE first, and then by distilling the amidated T3MBAEE wherein—due to their unexpected higher boiling points—the amide of T2MBAEE, optional T2MBAEE bisamide and optional T1MBAEE bisamide remain in the distillation residue. Furthermore, the amide of T2MBAEE, can also be separated from the mixture B, by distillation wherein—due to its unexpected higher boiling point—the optional amides of T2MBAEE and T1MBAEE remain in the distillation residue. Moreover, the T2MBAEE bisamide if present in mixture B, can also be isolated from said mixture B, by distillation of mixture B, T2MBAEE** bisamide remaining in the distillation residue.

For example, the formamide of T3MBAEE, which can be obtained by contacting mixture A with formic acid can be isolated from mixture B by distillation. When mixture B comprises T4MBAEE, T2MBAEE-formamide, optionally T2MBAEE-bisformamide and optionally T1MBAEE-bisformamides, T4MBAEE is first distilled (this compound having the lowest boiling point), and then T3MBAEE-formamide is distilled. Because of their unexpected higher boiling points T2MBAEE-formamide, optional T2MBAEE-bisformamide and optional T1MBAEE-formamides remain in the distillation residue. Once the T4MBAEE and T3MBAEE-formamide have been separated from mixture B, T2MBAEE-formamide can also be separated from mixture B by distillation. Because of their unexpected higher boiling point optional T2MBAEE-bisformamide and optional T1MBAEE-bisformamides remain in the distillation residue. Once the T4MBAEE, T3MBAEE-formamide and T2MBAEE-formamide have been separated from mixture B, T2MBAEE-bisformamide can also be isolated as a bottom residue from mixture B by distillation of mixture B.

In an embodiment, the difference between the boiling point of amidated N,N,N'-trimethylbisaminoethylether and the boiling point of a compound selected from the group comprising: N,N,N',N'-tetramethylbisaminoethylether, amidated N,N-dimethylbisaminoethylether, optional amidated N,N'-dimethylbisaminoethylether, and optional amidated N-monomethylbisaminoethylether, is at least 10° C.

According to a preferred embodiment of the present invention, the difference between the boiling point of amidated N,N,N'-trimethylbisaminoethylether, and the boiling point of amidated N,N-dimethylbisaminoethylether, at the same pressure, is of at least 10° C. Preferably the difference between the boiling point of N,N,N'-trimethylbisaminoethylether formamide, and the boiling point of N,N-dimethylbisaminoethylether formamide, at the same pressure, is of at least 10° C.

According to a preferred embodiment of the present invention, the difference between the boiling point of amidated N,N-dimethylbisaminoethylether and the boiling point of amidated N,N'-dimethylbisaminoethylether at the same pressure, is of at least 10° C. Preferably, the difference between the boiling point of N,N-dimethylbisaminoethylether formamide and the boiling point of N,N'-dimethylbisaminoethylether bisformamide at the same pressure, is of at least 10° C.

The next step in the method according to the first aspect to the invention comprises (c1) recovering N,N,N'-trimethylbisaminoethylether and/or (c2) recovering N, N dimethylbisaminoethylether from its amide preferably by means of a transamidation reaction.

(c1) Recovering N,N,N'-trimethylbisaminoethylether and/or (c2) recovering N, N dimethylbisaminoethylether from its amide may be obtained by the following steps:

transamidation of the amide; and separation of N,N,N'-trimethylbisaminoethylether and/or separation of N, N dimethylbisaminoethylether from the reaction mixture obtained in the transamidation step by fractionated azeotropic and/or fractionated non-azeotropic distillation.

In principle the transamidation of amidated T3MBAEE or T2MBAEE can be carried out by any technique known to the person skilled in the art. Preferably, transamidation of amidated T3MBAEE or T2MBAEE is carried out with a transamidation agent selected from the group comprising monoethanolamine, ammonia, primary and/or secondary amines, preferably with the proviso that the transamidation agent is not N,N,N'-trimethylbisaminoethylether, N,N-dimethylbisaminoethylether, N,N'-dimethylbisaminoethylether or N-monomethylbisaminoethylether.

Recovering N,N,N'-trimethylbisaminoethylether and/or N, N dimethylbisaminoethylether from its amide may be obtained by the following steps:

transamidation of the amide with a transamidation agent selected form the group comprising monoethanolamine, ammonia, primary and/or secondary amines with the proviso that the transamidation agent is not N,N,N'-trimethylbisaminoethylether, N,N-dimethylbisaminoethylether, N,N'-dimethylbisaminoethylether or N-monomethylbisaminoethylether; and separation of N,N,N'-trimethylbisaminoethylether and/or N, N dimethylbisaminoethylether from the reaction mixture obtained in the transamidation step by fractionated azeotropic and/or fractionated non-azeotropic distillation, preferably separation of N,N,N'-trimethylbisaminoethylether from the reaction mixture obtained in the transamidation step is performed by fractionated azeotropic distillation.

The transamidation agent may be selected from the group consisting of ammonia, primary and/or secondary amines. Preferred transamidation agents are presented by formula (1):

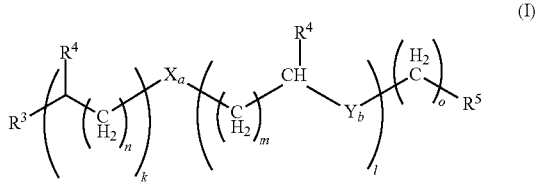

wherein
R³ is selected from the group comprising —H, —CH₃,

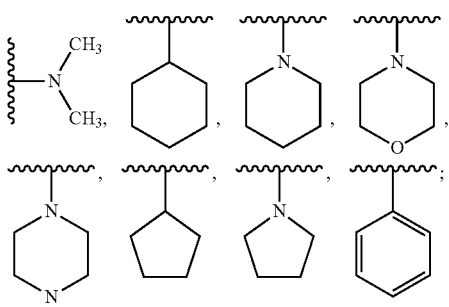

R⁴ is selected from the group comprising —H, —CH₃, ethyl, propyl, isopropyl, linear or branched C₄₋₁₂-alkyl;
R⁵ is selected from the group comprising R³, —OH, —NH₂, —OCH₃, —N(CH₃)₂;
each X and Y are selected from —O—, —NH—, —N(CH₃)—;
k is an integer selected from 0 to 35, preferably 1 to 20, more preferably 2 to 10;
l is an integer selected from 0 to 5;
m is 0 or 1;
n is integer selected from 0 to 30, preferably 1 to 24, more preferably 10 to 18;
o is 0 or 1;
a is 0 or 1; and
b is 0 or 1;
with the proviso that the transamidation agent comprises at least one nitrogen-hydrogen bond (N—H) and with the proviso that the transamidation agent is not N,N,N-trimethylbisaminoethylether, N,N-dimethylbisaminoethylether, N,N'-dimethylbisaminoethylether or N-monomethylbisaminoethylether.

Transamidation agents of formula (1) are preferred with k=1 and n=an integer from 10 to 30. In case n=0 or 1, k in formula (1) is preferably an integer from 1 to 35, more preferably k is an integer from 2 to 20.

Particularly, preferred transamidation agents are monoethanolamine, polyalkoxyleneamines or fatty amines. Preferred transamidation agents are primary or secondary alkanolamines. Primary alkanolamines can be selected from the group consisting of monoethanolamine, 1,3-propanolamine, isopropanolamine as well as C₄₋₈-alkanolamines. Secondary alkanolamines can be selected from the group consisting of diethanolamine, N-methylethanolamine, N-ethylethanolamine, N-propylethanolamine, N-isopropylethanolamine, N-methylisopropanolamine, N-ethylisopropanolamine, N-isopropylisopropanolamine, N—C₁₋₆-alkyl-N—C₂₋₆-alkanolamine, N,N-di-C₂₋₆-alkanolamine. Particularly, alkanolamines can be selected from the group consisting of monoethanolamine, 2(2-aminoethoxy)-ethanol, N-methylethanolamine, monoisopropanolamine, aminopropane-3-ol, N-ethyl ethanolamine, N-propylethanolamine, aminobutane-4-ol, N-2-hydroxyethylaniline, N-hydroxyethylpiperazine. The transamidation agent can also be selected from the group consisting of substituted and unsubstituted primary and/or secondary alkylamines or arylamines. The primary alkylamines are preferably selected from the group consisting of methylamine, ethylamine, propylamine, isopropylamine, cyclohexylamine, cyclopentylamine, C₄₋₁₈alkylamine, C₄₋₆-cycloalkylamine. The secondary alkylamines are preferably selected from the group consisting of dimethylamine, diethylamine, methylethylamine, C₁₋₆-alkyl-C₁₋₆-alkylamine, cycloaliphatic compounds comprising at least one nitrogen atom in the cycle such as pyrrolidone, piperazine, imidazoline and morpholine. Particularly, preferred are transamidation agents selected from the group consisting of monomethylamine, isopropylamine, aminobutane, aminooctane, amino dodecane, aminooctadecane, cyclohexylamine, N-methylcyclohexylamine, N-ethylcyclohexylamine, N,N-dicyclohexylamine, cyclopentylamine, N-methylcyclopentylamine, ethylcyclopentylamine, piperidine, pyrrolidine, aniline, 1,2-diaminoethane, diethylenetriamine, triethylenetetramine, bis-[3-(dimethylamino-propyl]-amine, N-aminoethylpiperazine, 1,3-dimethylaminopropane amine, 1-methoxypropane-3-amine, butoxypropane-3-amine, (2-dimethylaminoethoxy)-3-propanamine, morpholine, N-aminopropylmorpholine and aminoethoxyethylmorpholine. Further, ammonia, preferably aqueous ammonia is a suitable transamidation agent.

In the most preferred embodiment, the transamidation agent is monoethanolamine.

The transamidation agent is preferably present in excess relative to T3MBAEE-amide and/or T2MBAEE-amide. In a preferred embodiment the transamidation step is carried out essentially with T3MBAEE-amide and/or T2MBAEE and the transamidation agent such as monomethylamine without any further organic solvents present.

According to a preferred embodiment of the present invention, the transamidation in step (c1) and/or (c2) is carried out, with monomethylamine, as transamidation agent, by azeotropic distillation. In an embodiment, the azeotrope comprises monomethylamine, and N,N,N'-trimethylbisaminoethylether.

According to a preferred embodiment of the present invention, the transamidation in step (c1) and/or (c2) is carried out under reflux.

In some embodiment, the transamidation in step (c1) and/or (c2) can be carried out at a temperature ranging from 50 to 250° C. In a preferred embodiment the transamidation in step (c1) is carried out at a pressure ranging from 1 mbar to 500 mbar. In a preferred embodiment the transamidation in step (c1) is carried out at a reflux temperature of at least 100° C., preferably of at least 120° C., for example at least 125° C. or example at least 130° C., and preferably at a pressure of at least 100 mbar, for example of at least 200 mbar, for example of at least 250 mbar, for example of at least 300 mbar.

In an embodiment, after the transamidation, an azeotrope comprising N,N,N'-trimethylbisaminoethylether and/or an azeotrope comprising N,N dimethylbisaminoethylether and monoethanolamine, is obtained.

According to a preferred embodiment of the present invention, the azeotrope is distilled out during the transamidation process, preferably continuously distilled out. Preferably, said fractionated azeotropic distillation is carried out at a temperature from 50° C. to 250° C. Preferably, said fractionated azeotropic distillation is carried out at a pressure from 1 mbar to 500 mbar. Preferably, said fractionated azeotropic distillation is performed at a reflux temperature of least 100° C., preferably of at least 120° C., for example at least 125° C., for example at least 130° C., and preferably at a pressure of at least 100 mbar, for example at least 200 mbar, for example at least 250 mbar, for example at least 300 mbar.

In an embodiment, the azeotrope components are separated using a second azeotropic distillation using a hydrocarbon solvent. Non-limiting examples of suitable hydrocarbons solvents which can be used for this second azeotropic distillation include the solvents listed under the description of step (a) herein above. Preferred are hydrocarbons selected from the group comprising xylene, toluene, or methylcyclohexane. Most preferred are hydrocarbons selected from xylene, or methylcyclohexane.

The present invention also encompasses a method for separating N,N,N'-trimethylbisaminoethylether and/or N,N-dimethylbisaminoethylether, from a mixture A comprising N,N,N'-trimethylbisaminoethylether, and N,N-dimethylbisaminoethylether, wherein said method comprises the steps of:
(a) contacting said mixture A with an acylating agent, to form a mixture B comprising the amides of N,N,N'-trimethylbisaminoethylether and of N,N-dimethylbisaminoethylether, respectively;
(b1) separating the amide of N,N,N'-trimethylbisaminoethylether from mixture B; and (c1) recovering N,N,N'-trimethylbisaminoethylether from its amide by means of a transamidation reaction;
and/or
(b2) separating the amide of N,N-dimethylbisaminoethylether from mixture B; and (c2) recovering N,N-dimethylbisaminoethylether from its amide by means of a transamidation reaction. The embodiments described under steps (a), (a'), (b1), (b2), (c1), (c2), (i) of the methods according to the first aspect of the invention, apply mutatis mutandis to the steps of this present method.

According to the third aspect of the present invention, a method is provided for separating N,N'-dimethylbisaminoethylether from a mixture A comprising N,N,N'-trimethylbisaminoethylether, N,N'-dimethylbisaminoethylether, and N,N-dimethylbisaminoethylether, and optionally N,N,N',N'-tetramethylbisaminoethylether, and optionally N-monomethylbisaminoethylether. Said method comprises the steps of:
contacting said mixture A with an acylating agent, to form a mixture B comprising the amides of N,N,N'-trimethylbisaminoethylether, and N,N-dimethylbisaminoethylether and N,N'-dimethylbisaminoethylether, respectively;
separating the amide of N,N'-dimethylbisaminoethylether from said mixture B; and
recovering N,N'-dimethylbisaminoethylether from its amide by means of a transamidation reaction. The embodiments described under steps (a), (a'), (b1), (b2), (c1), (c2), (i)) of the methods according to the first aspect of the invention, apply mutatis mutandis to the steps of this present method.

The methods according to the present invention have the advantage that N,N,N'-trimethylbisaminoethylether may be obtained with a purity of more than 90%, for example more than 95%, for example more than 97.5%, such as more than 99%.

The methods according to the present invention have the further advantage that N,N-dimethylbisaminoethylether may be obtained with a purity of more than 90%, for example more than 95%.

The methods according to the present invention have the further advantage that N,N'-dimethylbisaminoethylether if present, may be obtained with a purity of more than 90%, for example more than 92%, for example more than 93%.

The present invention also encompasses a method for preparing N,N,N'-trimethylbisaminoethylether, comprising the steps of contacting 2-(2-dimethylaminoethoxy)-ethanol with monomethylamine in the presence of a catalyst, thereby obtaining a reaction mixture A comprising said N,N-dimethylbisaminoethylether and N,N,N'-trimethylbisaminoethylether, and separating N,N,N'-trimethylbisaminoethylether using a method according to the first aspect of the present invention.

According to the fourth aspect of the present invention, a method for preparing N,N-dimethylbisaminoethylether is provided. Said method comprises the step of contacting 2-(2-dimethylaminoethoxy)-ethanol with monomethylamine in the presence of a catalyst.

Non limiting examples of suitable catalysts include copper containing catalysts. Suitable catalysts can be selected from the group comprising copper chromite catalyst such as $CuO/Cr_2O_3$ catalyst, $2CuOxCr_2O_3$ (CAS#99328-50-4), $Cr_5CuO_5$ and the like; and $Cu/ZnO/Al_2O_3$ catalyst, and the like.

The step of contacting 2-(2-dimethylaminoethoxy)-ethanol with monomethylamine is preferably performed under pressure, for example at a pressure of at least 5 bar, for example at least 6 bar, for example at least 7 bar, for example at least 8 bar, for example at least 9 bar, for example at least 10 bar.

The present invention also encompasses the use of N,N,N'-trimethylbisaminoethylether, obtained according to the first aspect of the present invention as a precursor in the preparation of a catalysts useful for the production of polyurethane.

The present invention also encompasses the use of N,N-dimethylbisaminoethylether, obtained according to the first or third aspect of the present invention as catalyst in the production of polyurethane.

The present invention also relates to a method for preparing a compound selected from N,N-dimethylbisaminoethylether-monoformamide, N,N'-dimethylbisaminoethylether-bisformamide, and N-monomethylbisaminoethylether-bisformamide, by contacting a compound selected from N,N-dimethylbisaminoethylether, N,N'-dimethylbisaminoethylether, and N-monomethylbisaminoethylether, with formic acid.

The present invention further encompasses a compound selected from the group comprising N,N-dimethylbisaminoethylether-formamide and N,N'-dimethylbisaminoethylether-bisformamide, and N-monomethylbisaminoethylether-bisformamide.

The invention is illustrated but not limited by the following examples.

EXAMPLES

The examples described hereunder illustrate embodiments of the present invention.

In the examples the Area % was measured by gas chromatography (GC) and is based on the total Area of all peaks observed. The area % was obtained by first determining the area under each curve (Area=(height)×(width at ½ height)

and then by applying the following equation: Area % Component 1=[(area under peak 1)/(total area)]×100%.

Example 1

Preparation of Mixture A1

A 1000 ml fix bed adiabatic reactor was charged with 1000 cm³ of copper chromite catalyst. 2-(2-dimethylaminoethoxy)-ethanol (CAS#1704-62-7) (also referred as Jeffcat ZR-70, commercially available from Huntsman) and monomethylamine (MMA) (commercially available, CAS #74-89-5) were charged to the reactor at different reaction conditions, as shown in Table 1. The reactor effluents were taken off the reactor, depressurized, degassed and collected for analysis and further use. Running conditions and compositions of the reactor effluents are shown in Table 1.

TABLE 1

Running conditions and composition of mixtures A1.

|  | unit | Run 1 | Run 2 | Run 3 | Run 4 | Run 5 | Run 6 | Run 7 |
| --- | --- | --- | --- | --- | --- | --- | --- | --- |
| Reaction Conditions |  |  |  |  |  |  |  |  |
| Reaction time | hours | 19 | 42 | 164 | 355 | 513 | 571 | 642 |
| MMA/ZR-70 molar ratio |  | 2.21 | 1.15 | 0.81 | 0.42 | 0.99 | 0.96 | 4.74 |
| Reactor temperature | ° C. | 194 | 192 | 182 | 184 | 166 | 166 | 165 |
| Reactor pressure | bar | 10 | 10 | 10 | 10 | 10 | 10 | 10 |
| ZR-70 feed | g/h | 254 | 252 | 253 | 244 | 103 | 106 | 251 |
| MMA feed | g/h | 130.7 | 67.3 | 47.52 | 23.76 | 23.76 | 23.76 | 27.72 |
| Mixture A1 composition |  |  |  |  |  |  |  |  |
| MMA + DMA + TMA | Area % | 1.75 | 0.30 | 0.10 | 0.03 | 0.14 | 2.34 | 13.30 |
| N-methylmorpholine | Area % | 5.84 | 5.17 | 2.88 | 5.01 | 1.60 | 2.48 | 0.21 |
| Morpholine | Area % | 0.35 | 0.33 | 0.11 | 0.19 | 0.04 | 0.07 | 0.00 |
| T4MBAEE | Area % | 9.36 | 8.91 | 4.96 | 8.45 | 19.37 | 3.87 | 0.40 |
| T3MBAEE | Area % | 29.27 | 32.52 | 26.89 | 20.25 | 26.81 | 28.70 | 23.44 |
| T2MBAEE | Area % | 1.02 | 1.12 | 0.60 | 0.44 | 0.46 | 0.53 | 0.13 |
| T1MBAEE | Area % | 0.12 | 0.13 | 0.05 | 0.03 | 0.03 | 0.04 | 0.00 |
| Jeffcat-ZR 70 | Area % | 38.25 | 37.08 | 54.32 | 52.25 | 44.03 | 53.52 | 59.23 |
| Other compounds | Area % | 14.04 | 14.44 | 10.09 | 13.35 | 7.52 | 8.45 | 3.29 |

TMA = trimethylamine

Example 2

Preparation of Mixture A2

About 55 liter of the crude reactor product (mixture A1) of Example 1 was distilled to remove the majority of ZR70. This distillation was repeated four times, resulting each time, in a mixture of amines containing more than 60% N,N,N'-trimethylbisaminoethylether (T3MBAEE), about 20% N,N,N',N'-tetramethylbisaminoethylether (T4MBAEE). Further investigation showed the presence of significant quantities of N,N-dimethylbisaminoethylether (T2MBAEE), N,N'-dimethylbisaminoethylether (T2MBAEE**) and N-monomethylbisaminoethylether (T1MBAEE). The reaction conditions and the composition of the resulting mixture (analyzed by GC-MS) are shown in Table 2.

TABLE 2

Composition of mixtures A2.

| Mixture A2 composition | | Quantity | | | |
| --- | --- | --- | --- | --- | --- |
| | g | 5650 | 5875 | 5728 | 3797 |
| N-methylmorpholine | Area % | 0.42 | 0.41 | 0.42 | 11.01 |
| Morpholine | Area % | 0.91 | 0.90 | 0.93 | 0.53 |
| T4MBAEE | Area % | 19.70 | 19.49 | 19.82 | 20.62 |
| T3MBAEE | Area % | 63.54 | 63.95 | 63.72 | 61.08 |
| T2MBAEE | Area % | 9.59 | 9.69 | 9.57 | 1.87 |
| T2MBAEE** | Area % | 3.64 | 3.64 | 3.54 | 1.54 |
| 2-(2-dimethylaminoethoxy)-ethanol | Area % | 0.05 | 0.01 | 0.04 | 1.70 |
| Other compounds + T1MBAEE | Area % | 2.15 | 1.91 | 1.96 | 1.65 |

Example 3

Acylation of Mixture A2, Run 1, of Example 2 and Subsequent Separation of T3MBAEE-formamide 4900 g of mixture A2, Run 1 of Example 2 and 1000 g methylcyclohexane (MCH) were charged into a 10 liter round-bottomed flask. The flask was heated up to 85° C. and 1620 g of technical formic acid (85 wt. %) was pumped into the flask (8 g/min). Thereafter the mixture was heated up to reflux. The water/MCH azeotrope formed was continuously removed. While the MCH phase was recycled to the reaction flask, the formed water was taken away. After the water formation stopped, the MCH and some light boiling contaminants were distilled out until the flask temperature reached 190° C. The remaining bottom-product was used for the subsequent vacuum distillation. GC analysis of the crude material (mixture B1)), showed the presence of the formamides as presented in Scheme 2.

Scheme 2

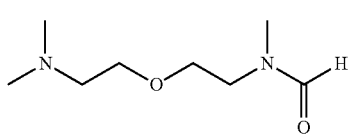

"T3-formamide"

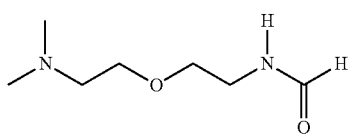

T2-formamide

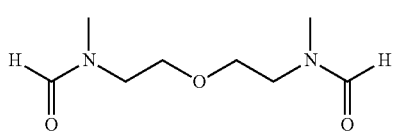

T2**-formamide 2

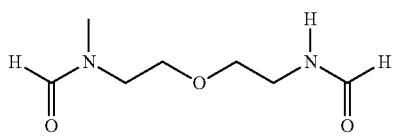

T1-formamide 3

The conditions and results of the distillation of reaction mixture B1 are shown in Table 3.

Unexpectedly, distillation of the formylation reaction product, resulted in the separation of 1.7 kg of practically pure N,N,N'-trimethylbisaminoethylether-formamide (T3MBAEE mono-formamide) by combination of fractions 5, 6 and 7.

Example 4

Acylation of Mixture A2, (Run 1 of Example 2) and Subsequent Isolation of N,N,N'-trimethyl-bisaminoethylether formamide (T3MBAEE-formamide), N,N-dimethylbisaminoethylether formamide (T2MBAEE-formamide) and N,N'-dimethyl-bisaminoethylether bisformamide (T2MBAEE**-bisformamide)

Step 1: Acylation of Mixture A2 (Run 1 of Example 2)

In an typical run, 4700 g of reaction mixture A2, Run 1, (prepared as described in Example 2 and having the composition shown in Table 4), were mixed with 1450 ml of MCH and filled in to a 10 liter distillation flask connected to a 1 m distillation column, packed with SULZER® EX packing, equipped with a magnet-coupled stirrer, heating mantle, automatic phase separator and a feed pump. 1600 g of formic acid (85% solution in water) was added at a flow rate of 450 g/h to the distillation flask. After complete addition of the formic acid the reaction mixture was heated up to reflux. The water/MCH azeotrope formed, was continuously removed. While the MCH phase was recycled to the reaction flask, the formed water was taken away. After the water separation stopped the MCH was distilled out, at atmospheric pressure, until the temperature in the reaction

TABLE 3

Composition, conditions and results of the distillation of reaction mixture B

| Sample name | Mixture B1 | Fraction 1 | Fraction 2 | Fraction 3 | Fraction 4 | Fraction 5 | Fraction 6 | Fraction 7 | Residue |
|---|---|---|---|---|---|---|---|---|---|
| Boiling range, head temperature ° C. | | 23-39.5 | 70.5-71.5 | 136.5 | 136.5 | 138.5-139 | 139 | 139-139.5 | |
| Boiling range, pot temperature ° C. | | 38.5-154.5 | 100-146.0 | 147.5 | 148.5 | 148.5-149.5 | 150-153 | 153.5-169 | |
| Pressure mbar | | 100 | 10 | 10 | 10 | 10 | 10 | 10 | 10 |
| Reflux take off ratio | | 1:1 | 5:1 | 5:1 | 5:1 | 5:1 | 5:1 | 5:1 | |
| Quantity [g] | 3000 | 222 | 481.4 | 45.9 | 22.5 | 4 | 951.2 | 744.1 | 472.4 |
| Composition | all values in area % | | | | | | | | |
| Methylcyclohexane | 19.34 | 99.58 | 5.4 | 0 | 0 | 0 | 0 | 0 | |
| N-methyl-morpholine | 0 | 0.01 | 0.03 | 0 | 0 | 0 | 0 | 0 | |
| Morpholine | 0 | 0 | 0 | 0 | 0 | 0 | 0 | 0 | |
| T2+2-(2-dimethylamino ethoxy)-ethanol | 0.48 | 0 | 2.85 | 2.07 | 0.57 | 0.17 | 0.23 | 0.3 | |
| T3 | 1.15 | 0 | 6.08 | 1.61 | 0.52 | 0.15 | 0.19 | 0.12 | |
| T4 | 16.61 | 0 | 85.01 | 36.05 | 3.24 | 0.07 | 0.1 | 0 | |
| T3 mono-formamide | 46.89 | 0 | 0 | 26.21 | 81.2 | 99.1 | 98.4 | 99.34 | 9.8 |
| T2 mono-formamide | 0 | 0 | 0 | 0 | 0 | 0 | 0 | 0 | 60.6 |
| T2* diformamide | 0 | 0 | 0 | 0 | 0 | 0 | 0 | 0 | 18.2 |
| T1 diformamide | 0 | 0 | 0 | 0 | 0 | 0 | 0 | 0 | 8.8 |
| Other | 15.53 | 0.41 | 0.79 | 34.06 | 14.47 | 0.51 | 1.08 | 0.24 | 2.6 | flask reached ~187 to 190° C. The reaction mixture B2 thereby obtained was allowed to cool off, for analytical investigation by gas chromatography, but also for subsequent vacuum distillation. GC analysis showed the composition given in Table 5. The reported numbers are area % by GC

TABLE 4

Composition of mixture A2, Run 1.

| Mixture composition | area % by GC |
| --- | --- |
| N-methylmorpholine | 0.42 |
| morpholine | 0.91 |
| N,N,N',N'-tetramethylbisaminoethylether | 19.7 |
| N,N,N'-trimethylbisaminoethylether | 63.54 |
| N,N-dimethylbisaminoethylether | 9.59 |
| N,N'-dimethylbisaminoethylether | 3.64 |
| Σ dimethylaminoethoxyethanol/diethyleneglycol | 0.05 |
| Other compounds | 2.15 |

TABLE 5-continued

Composition of mixture B2.

| Mixture B2 composition | area % by GC |
| --- | --- |
| N,N,N'-trimethylbisaminoethylether formamide | 50.43 |
| N,N-dimethylbisaminoethylether formamide | 10.67 |
| Σ dimethylaminoethoxyethanol/diethyleneglycol | 0.04 |
| Other compounds | 3.13 |

Step 2: Vacuum Distillation of Mixture B2 and Isolation of Pure N,N,N'-trimethylbisaminoethylether formamide and pure N,N-dimethylbisaminoethylether-formamide In a typical run, 3207 g of mixture B2 were charged into a 4 liter distillation flask connected to a 1 m distillation column, packed with SULZER® EX packing's. At the start of the process, the pressure was set to 100 mbar at which pressure, the majority of MCH and some other light-boiling materials were removed. When the flask temperature reached about 156° C., the distillation flask was cooled down, the pressure was reduced stepwise, to a pressure of 4 mbar, and the fractionation started. The conditions and results of the distillation of reaction mixture B2 are shown in Table 6.

TABLE 6

Conditions and results of the distillation of reaction mixture B2

| | | distillation condition at fraction | | | | | | | |
| --- | --- | --- | --- | --- | --- | --- | --- | --- | --- |
| Description | feedstock | 1 | 2 | 3 | 4 | 5 | 6 | 7 | Residue |
| Vacuum distillation of mixture B2 | | | | | | | | | |
| Head temperature, ° C., max. | | 118 | 61 | 120 | 120.5 | 120.5 | 137 | 137 | |
| Head temperature, ° C., min. | | 25.5 | 28 | 60 | 120 | 120 | 123 | 136.5 | |
| Pot temperature, ° C., max. | | 156.5 | 124 | 141 | 142 | 158 | 161.5 | 209.5 | |
| Pot temperature, ° C., min. | | 22.5 | 53 | 130 | 141 | 151 | 157.5 | 201 | |
| Pressure, mbar | | 100 | 6* | 6* | 4 | 4 | 4 | 4 | |
| Reflux/take-off ratio | | 1:1 | 1:1 | 5:1 | 5:1 | 5:1 | 5:1 | 5:1 | |
| Quantity, g | 3207 | 223.5 | 334 | 200.5 | 875.5 | 928 | 156.4 | 178.1 | 240 |
| Composition of fraction by area % according to GC | | | | | | | | | |
| Methylcyclohexane (MCH) | 17.25 | 94.76 | 0.09 | 0 | 0 | 0 | 0 | 0.01 | |
| N-methylmorpholine | 0.14 | 1.19 | 0.03 | 0.04 | 0 | 0 | 0 | 0 | |
| Morphholine | | 0 | 0 | 0 | 0 | 0 | 0 | 0 | |
| Σ dimethylaminoethoxyethanol + diethyleneglycol | 0.04 | 0.02 | 0.3 | 0.2 | 0.04 | 0.1 | 0.4 | 0.15 | |
| N,N,N'-trimethylbisaminoethylether | 0.09 | 0.08 | 0.47 | 0.27 | 0.05 | 0.05 | 0.03 | 0.01 | |
| N,N,N',N'-tetramethylbisaminoethylether | 18.33 | 3.14 | 98.85 | 68.95 | 0.08 | 0.01 | 0.01 | 0.02 | |
| N,N,N'-trimethylbisaminoethylether-formamide | 50.34 | 0.02 | 0.1 | 18.89 | 99.27 | 99.7 | 26.18 | 0.9 | |
| N,N-dimethylbisaminoethylether-formamide | 10.67 | 0 | 0 | 0 | 0 | 0 | 68.22 | 98.55 | |
| Σ others | 3.13 | 0.79 | 0.26 | 11.65 | 0.56 | 0.14 | 5.16 | 0.36 | |

*= vacuum was not stable, 4-6 mbar
*= 4-6 mbar

TABLE 5

Composition of mixture B2.

| Mixture B2 composition | area % by GC |
| --- | --- |
| methylcyclohexane | 17.25 |
| N-methylmorpholine | 0.14 |
| morpholine | 0.01 |
| N,N,N',N'-tetramethylbisaminoethylether | 18.33 |
| N,N,N'-trimethylbisaminoethylether | 0.09 |

Unexpectedly, distillation of mixture B2 resulted in the separation of about 1.8 kg of practically pure (~99.5% purity) N,N,N'-trimethylbisaminoethylether-formamide (T3MBAEE formamide) by combination of fractions 4 and 5; and the recovery of 178.1 g of practically pure (~98.6%) N,N-dimethylbisaminoethylether-formamide (T2MBAEE-monoformamide) from fraction 7.

As it can be seen from the protocol in Table 6, pure N,N,N'-trimethylbisaminoethylether formamide (~99.5% purity) was collected at a head temperature of 120° C. to 120.5° C. at a pressure of 4 mbar, whereas pure N,N- dimethylbisaminoethylether-formamide (~98.6%) was collected at a head temperature 16° C. to 16.5° C. higher at 136.5° C. to 137° C., also at a pressure of 4 mbar. This indicates a difference in boiling point of the 2 materials. Both materials were at ambient temperature found to be water-white, clear liquids, having a characteristic odor.

Step 3: Recovery of Pure
N,N'-dimethylbisaminoethylether bisformamide
from residues of the vacuum distillation of mixture
B2

Acylation of a mixture A2 and subsequent distillation of the resulting mixture B2 were repeated several time and the distillation residues from these experiments were collected and pooled together to form mixture C having the composition shown in Table 7.

TABLE 7

| Composition of mixture C | |
|---|---|
| Composition | area % by GC |
| N,N,N'-trimethylbisaminoethylether formamide | 5.54 |
| N,N-dimethylbisaminoethylether formamide | 64.1 |
| N,N'-dimethylbisaminoethylether bisformamide | 30.0 |
| Σ other compounds | 0.4 |

Step 3a: Isolation of Light-boiling Components
from Mixture C 3010 g of mixture C were charged into a 4 liter distillation flask connected to a 1 m distillation column, packed with SULZER® EX packing. The pressure was set to 4 mbar and the distillation started at a reflux/take-off ratio of 5:1 to isolate N,N-dimethylbisaminoethylether formamide, the head input was set 20% higher than previously described. The head temperature was allowed to go to 142° C., and in parallel the pot temperature was allowed to go up to 220° C. The conditions and results of the distillation of mixture C are shown in Table 8.

The distillation, as shown in Table 8, afforded 1521 g N,N-dimethylbisaminoethylether formamide (T2MBAEE-formamide), with a purity of 96.1% (area % by GC) and 1217 g of a N,N'-dimethylbisaminoethylether bisformamide (T2MBAEE**-bisformamide)-rich residue.

Step 3b: Flash Distillation of Residue Obtained
from Step 3a 1217 g of the N,N'-dimethylbisaminoethylether bisformamide (T2MBAEE**-bisformamide)-rich residue obtained from step 3a was charged to a 2 liter distillation flask fitted with an electrically heating jacket, thermometer, magnetic stirrer, and a splash protection device of 15 cm length, filled with stainless steel mesh rings. The splash protection device was connected to a Liebig condenser with a receiver flask. Vacuum was connected, and the flash distillation started. The conditions and results of the flash distillation of distillation residue are shown in Table 9.

TABLE 9

Conditions and results of the flash distillation of the
N,N'-dimethylbisaminoethylether bisformamide
(T2MBAEE**-bisformamide)-rich residue

| | Flash distillation of N,N'-dimethylbisaminoethylether bisformamide-rich residue | | |
|---|---|---|---|
| | | distillation condition at fraction | |
| Description | feedstock | 1 | residue |
| Head temperature, ° C., max. | | 198 | — |
| Head temperature, ° C., min. | | 157 | — |
| Pot temperature, ° C., max. | | 220 | 220 |
| Pot temperature, ° C., min. | | 22.5 | 22.5 |
| Pressure, mbar | | 4 | 4 |
| Quantity, g | 1217 | 798.3 | 401 |

TABLE 8

Conditions and results of the distillation of reaction mixture C.
Vacuum distillation of mixture C

| | | distillation condition at fraction | | | | |
|---|---|---|---|---|---|---|
| Description | feedstock | 1 | 2 | 3 | 4 | residue |
| Head temperature, ° C., max. | | 137 | 139 | 140 | 142 | |
| Head temperature, ° C., min. | | 120 | 137 | 139 | 140 | |
| Pot temperature, ° C., max. | | 167.5 | 169 | 191 | 220 | |
| Pot temperature, ° C., min. | | 22.5 | 167.5 | 169 | 191 | |
| Pressure, mbar | | 4 | 4 | 4 | 4 | |
| Reflux/take-off ratio | | 5:1 | 5:1 | 5:1 | 5:1 | |
| Quantity, g | 3010 | 199.6 | 552 | 520.4 | 448.6 | 1217 |
| Composition of fraction by area % according to GC | | | | | | |
| | feedstock | 1 | 2 | 3 | 4 | residue |
| N,N,N'-trimethylbisaminoethylether-formamide | 5.54 | 35.31 | 0.78 | 0.35 | 0.44 | n.d. |
| N,N-dimethylbisaminoethylether-formamide | 64.1 | 51.55 | 95.0 | 96.5 | 97.3 | n.d. |
| N,N'-dimethylbisaminoethylether-bisformamide | 30.0 | 0 | 0 | 0 | 0 | n.d. |
| Σ others | 0.4 | 13.1 | 4.2 | 3.2 | 2.3 | n.d. |

TABLE 9-continued

Conditions and results of the flash distillation of the
N,N'-dimethylbisaminoethylether bisformamide
(T2MBAEE**-bisformamide)-rich residue

| | Composition of fraction by area % according to GC | | |
|---|---|---|---|
| | feedstock | 1 | residue |
| N,N,N'-trimethylbisaminoethylether-formamide | n.d. | 1.02 | 0.02 |
| N,N-dimethylbisaminoethylether-formamide | n.d. | 13.64 | 0.05 |
| N,N'-dimethylbisaminoethylether-bisformamide | n.d. | 74.3 | 94.5 |
| Σ others | n.d. | 12.0 | 4.9 |

Since Fraction 1 (Table 9) contained more than 70% (area % by GC) of N,N'-dimethylbisaminoethylether bisformamide (T2MBAEE**-bisformamide), this fraction was again subjected to flash distillation, as previously described. The conditions and results of the re-distillation of Fraction 1 are shown in Table 10.

TABLE 10

Conditions and results of the re-distillation of Fraction 1.

| | Flash distillation of Fraction 1 | | |
|---|---|---|---|
| Description | feedstock | distillation condition at fraction 1 | residue |
| Head temperature, ° C., max. | | 197 | — |
| Head temperature, ° C., min. | | 127 | — |
| Pot temperature, ° C., max. | | 207 | 207 |
| Pot temperature, ° C., min. | | 22.5 | 22.5 |
| Pressure, mbar | | 2.7 | 2.7 |
| Quantity, g | 798.3 | 225.3 | 553.7 |

| | Composition of fraction by area % according to GC | | |
|---|---|---|---|
| | feedstock | 1 | residue |
| N,N,N'-trimethylbisaminoethylether-formamide | 1.02 | 2.17 | 0.38 |
| N,N-dimethylbisaminoethylether-formamide | 13.64 | 38.48 | 0.24 |
| N,N'-dimethylbisaminoethylether-bisformamide | 74.3 | 43.3 | 93.9 |
| Σ others | 12.0 | 16.0 | 5.5 |

The procedures described in step 3b resulted in the recovery of 954 g of N,N'-dimethylbisaminoethylether bisformamide (T2MBAEE**-bisformamide) as a bottom product having a purity of about 94% (area % by GC). The boiling of N,N'-dimethylbisaminoethylether bisformamide can be estimated to be ranging between 198° C. and 205° C. at a pressure of about 1 mbar.

Example 5

Recovery of N,N,N'-trimethylbisaminoethylether (T3MBAEE) from N,N,N'-trimethylbisaminoethylether-formamide Step 1: Transamidation of N,N,N'-trimethylbisaminoethylether-formamide by monoethanolamine 3540 g of N,N,N'-trimethylbisaminoethylether-formamide (T3MBAEE-monoformamide) (purity by GC 99.25 area %; about 20.16 mol) obtained as described in examples 3 and 4, and 4960 g of monomethylamine (purity by GC 99.20 area %; about 80.55 mol) were charged into a 10 liter distillation flask connected to a 2 m distillation column, packed with SULZER® DX packing. The resulting mixture was heated to reflux under a 300 mbar vacuum. 300 g light boiling materials were collected as an over-head product before the head temperature reached 128.5° C. At this temperature the collection of the main fraction was started. Thereafter, the head temperature stabilized quickly at 130.5 to 131.5° C. at a reflux/take-off ratio of 10:1. A sudden rise of the head temperature by 3 to 3.5° C. indicated the end-point of the transamidation reaction. Up to this point about 4950 g as the main-fraction were collected. The composition of the resulting main fraction (analyzed by GC) is shown in Table 11.

TABLE 11 typical composition of the
N,N,N'-trimethylbisaminoethylether/monoethanolamine - azeotrope

| Composition, | area % by GC |
|---|---|
| methycyclohexane | 0 |
| monoethanolamine | 39.0 to 39.3 |
| N-methylmorpholine | 0 to 0.05 |
| morpholine | 0 to 0.05 |
| Σ dimethylaminoethoxyethanol/diethyleneglycol | 0.15 to 0.20 |
| N,N,N'-trimethylbisaminoethylether | 60.1 to 60.7 |
| N,N,N',N'-tetramethylbisaminoethylether | 0.01 to 0.02 |
| N,N-dimethylbisaminoethylether-formamide | 0 |
| N,N,N'-trimethylbisaminoethylether-formamide | 0 to 0.02 |
| Σother compounds | 0.15 to 0.50 |

Analysis of the distillation residue showed that it was essentially free of N,N,N'-trimethylbisaminoethylether-formamide (T3MBAEE-formamide).

Step 2: Splitting of the N,N,N'-trimethylbisaminoethylether/monoethanolamine azeotrope (T3MBAEE/MEA-azeotrope)

In a typical run, 4000 g of xylene (mixture of isomers) were charged into a 10 liter distillation flask connected to a 2 m distillation column, packed with SULZER® DX packing. An automatic phase separator for recycle of the xylene was fitted to the column head and the heat was set to ensure 2500 g/h flow on the column under atmospheric conditions.

When the xylene appeared on the head, the T3MBAEE/MEA-azeotrope mixture (product of Step 1) was fed by pumping continuously in to the distillation flask. The flow rate was adjusted to about 280 g/h at a reflux/take-off ratio of 0.6:1. The total feed quantity was typically 6000 to 6500 g of T3MBAEE/MEA-azeotrope. By this procedure the heterogeneous xylene(s)/monoethanolamine azeotropes were distilling to the head. After phase separation, the xylene-isomer mixture was recycled to the distillation flask whereas the monoethanolamine phase was collected separately. After the end of the separation of monoethanolamine, the bottom temperature of the distillation flask was increased up to 170° C. to remove the majority of the xylene under atmospheric conditions.

The bottom product contained essentially N,N,N'-trimethylbisaminoethylether and xylene, only. Typically it was almost free of MEA. The composition of the bottom product is shown in Table 12.

TABLE 12

Typical composition of the N,N,N'-trimethylbisaminoethylether/xylene - solution

| composition | area % by GC |
| --- | --- |
| N,N,N'-trimethylbisaminoethylether | 53 to 56 |
| xylene | 43 to 47 |
| monoethanolamine | ≤0.01 |

Step 3: Purification of N,N,N'-trimethylbisaminoethylether

In a typical run about 7 kg of N,N,N'-trimethylbisaminoethylether/xylene solution (product of step 2) were charged into a 10 liter distillation flask connected to a 2 m distillation column, packed with SULZER® DX packing's. The pressure was set to 100 mbar and the distillation started. Xylene was recovered at a head temperature of 73 to 74° C. and a reflux/take-off ratio of 2:1. After the head temperature started to rise, the reflux/take-off ratio of 2:1 was increased to 5:1. A transition fraction was taken until the head temperature stabilized at 118° C. At those conditions 3.5 to 4 kg of pure N,N,N'-trimethylbisaminoethylether as a product fraction was collected, depending on the starting concentration of the xylene solution. The typically composition of such a product is shown in table 13.

TABLE 13

Typical composition of the N,N,N'-trimethylbisaminoethylether

| Composition | area % by GC |
| --- | --- |
| methycyclohexane | 0.00 |
| xylene | 0.03 |
| monoethanolamine | 0.01 |
| Σ dimethylaminoethoxyethanol/diethyleneglycol | 0.24 |
| N,N,N'-trimethylbisaminoethylether | 99.3 to 99.6 |
| N,N,N',N'-tetramethylbisaminoethylether | 0.03 |
| N,N-dimethylbisaminoethylether-formamide | 0.00 |
| N,N,N'-trimethylbisaminoethylether-formamide | 0.00 |
| Σ other compounds | 0.15 to 0.40 |

Example 6

Recovery of N,N'-dimethylbisaminoethylether (T2MBAEE) from N,N'-dimethylbisaminoethylether bisformamide (T2MBAEE-bisformamide)

Step 1: Transamidation of N,N'-dimethylbisaminoethylether bisformamide by monoethanolamine 940 g of N,N'-dimethylbisaminoethylether bisformamide (T2MBAEE**-bisformamide) (purity by GC 94.1 area %; about 4.7 mol) prepared as described in Example 4 and 2400 g of monoethanolamine (purity by GC 99.20 area %, about 40 mol) were charged in to a 4 liter distillation flask connected to a 1 m distillation column, packed with SULZER® EX packing. The mixture was heated to reflux under a 300 mbar vacuum. 133 g of light boiling materials were collected as an overhead product before the head temperature reached 134° C. At this temperature the collection of the main fraction was started. Thereafter, the head temperature stabilized quickly at 136 to 137° C. at a reflux/take-off ratio of 10:1. A sudden rise of the head temperature by 3 to 3.5° C. indicated the end-point of the transamidation reaction. Up to this point about 1135 g as the main-fraction were collected. The analysis of a main-fraction by gas chromatography gave the composition as shown in Table 14

TABLE 14

Composition of the N,N'-dimethylbisaminoethylether/monoethanolamine - azeotrope

| Composition | area % by GC |
| --- | --- |
| methycyclohexane | 0.00 |
| monoethanolamine | 62.94 |
| Σ dimethylaminoethoxyethanol/N,N-dimethylbisaminoethylether | 0.57 |
| N,N'-dimethylbisaminoethylether | 34.01 |
| N,N,N'-trimethylbisaminoethylether | 1.07 |
| N,N-dimethylbisaminoethylether-formamide | 0.00 |
| N,N,N'-trimethylbisaminoethylether-formamide | 0.00 |
| N,N'-dimethylbisaminoethylether-bisformamide | 0.00 |
| Σother compounds | 1.41 |

Step 2: Splitting of the N,N'-dimethylbisaminoethylether/monoethanolamine azeotrope 1500 g xylene (mixture of isomers) and 1070 g N,N'-dimethylbisaminoethylether/MEA were charged into a 4 liter distillation flask connected to a 1 m distillation column, packed with SULZER® DX packing's. A half-automatic phase separator for recycle of the xylene was fitted to the column head and the distillation under atmospheric conditions started.

By this procedure the heterogeneous xylene(s)/monoethanolamine azeotropes were distilling to the head. After phase separation the xylene-isomer mixture was recycled to the distillation flask whereas the monoethanolamine phase was collected separately. After the end of the separation of the monoethanolamine, the bottom temperature of the distillation flask was increased up to 170° C. to remove a majority of the xylene under atmospheric conditions. The composition of the N,N'-dimethylbisaminoethylether/xylene solution is shown in Table 15.

TABLE 15

Composition of the N,N'-dimethylbisaminoethylether/xylene solution

| Composition | area % by GC |
| --- | --- |
| monoethanolamine | 0.17 |
| Σ dimethylaminoethoxyethanol/ N,N-dimethylbisaminoethylether | 1.14 |
| N,N'-dimethylbisaminoethylether | 29.34 |
| N,N,N'-trimethylbisaminoethylether | 2.19 |
| N,N-dimethylbisaminoethylether-formamide | 0 |
| N,N,N'-trimethylbisaminoethylether-formamide | 0 |
| N,N'-dimethylbisaminoethylether-bisformamide | 0 |
| xylene | 65.57 |
| Σother compounds | 1.59 |

Step 3: Purification of N,N'-dimethylbisaminoethylether 1730 g N,N'-dimethylbisaminoethylether/xylene solution (product of step 2) were charged into a 4 liter distillation flask connected to a 1 m distillation column, packed with SULZER® EX packing's. The pressure was set to 100 mbar and the distillation started. Xylene was recovered at head temperature of 73 to 74° C. and a reflux/take-off ratio of 2:1. After the head temperature started to rise, the reflux/take-off ratio of 2:1 was increased to 5:1. A transition fraction of about 50 g was taken and the head temperature stabilized at 83° C. Under this condition, 222.1 g of N,N'-dimethylbisaminoethylether as a product fraction were collected. The composition of this product fraction is shown in Table 16.

TABLE 16

Purification of N,N'-dimethylbisaminoethylether

| Composition | area % by GC of fraction | |
|---|---|---|
| | 1 | 2 |
| quantity of fraction [g] | 50 | 222.1 |
| monoethanolamine | 0.17 | 0.19 |
| Σ dimethylaminoethoxyethanol/diethyleneglycol/N,N-dimethylbisaminoethylether | 1.14 | 1.21 |
| N,N'-dimethylbisaminoethylether | 29.34 | 94.29 |
| N,N,N'-trimethylbisaminoethylether | 2.19 | 2.11 |
| N,N'-dimethylbisaminoethylether-bisformamide | 0 | 0 |
| Σother compounds | 1.59 | 2.20 |

Example 7

Recovery of N,N-dimethylbisaminoethylether (T2MBAEE) from N,N-dimethylbisaminoethylether formamide (T2MBAEE-formamide)

Step 1: Transamidation of N,N-dimethylbisaminoethylether-formamide by monoethanolamine 448.7 g of N,N-dimethylbisaminoethylether-formamide (T2MBAEE-monoformamide) (purity by GC 97.31 area %; about 3.4 mol) obtained as described in examples 3 and 4, and 1300 g of monoethanolamine (purity by GC 99.20 area %; about 21.1 mol) were charged into a 2 liter distillation flask connected to a 1 m distillation column, packed with SULZER® EX packing. The resulting mixture was heated to reflux under a 300 mbar vacuum. The material was collected as an over-head product after the head temperature reached 134° C. at a reflux ratio of 10:1. The composition of the product mixture is shown in Table 17.

TABLE 17 typical composition of the N,N-dimethylbisaminoethylether/monoethanolamine - azeotrope

| Composition, | area % by GC |
|---|---|
| monoethanolamine | 82.0 |
| N,N-dimethylbisaminoethylether | 20.6 |
| N,N,N'-trimethylbisaminoethylether | 0.01 |
| N,N'-dimethylbisaminoethylether | 0.04 |
| Σother compounds | 2.3 |

Step 2: Splitting of the N,N-dimethylbisaminoethylether/monoethanolamine azeotrope (T2MBAEE/MEA-azeotrope)

1900 g of xylene (mixture of isomers) and the N,N-dimethylbisaminoethylether/monoethanolamine azeotrope were charged into a 4 liter distillation flask connected to a 1 m distillation column, packed with SULZER® EX packing. An automatic phase separator for recycle of the xylene was fitted to the column head and the distillation was started under atmospheric conditions.

By this procedure the heterogeneous xylene(s)/monoethanolamine azeotropes were distilling to the head. After phase separation, the xylene-isomer mixture was recycled to the distillation flask whereas the monoethanolamine phase was collected separately. After the end of the separation of monoethanolamine, the bottom temperature of the distillation flask was increased up to 140° C. to remove the majority of the xylene under atmospheric conditions.

The bottom product contained essentially N,N-dimethylbisaminoethylether and xylene, only. It was practically free of MEA.

Step 3: Purification of N,N-dimethylbisaminoethylether

The N,N-dimethylbisaminoethylether/xylene solution (product of step 2) was charged into a 4 liter distillation flask connected to a 1 m distillation column, packed with SULZER® EX packing's. The pressure was set to 100 mbar and the distillation started. Xylene was recovered at a head temperature of 73 to 74° C. and a reflux/take-off ratio of 2:1. After the completion of the xylene removal the pressure was reduced down to 20 mbar. After a short transition fraction the head temperature stabilized at 79.5° C. and the product fraction was collected at reflux ratio of 5:1. The composition of the product fraction is shown in Table 18.

TABLE 18

Typical composition of the N,N-dimethylbisaminoethylether

| Composition | area % by GC |
|---|---|
| xylene | 2.52 |
| monoethanolamine | 1.01 |
| N,N,N'-trimethylbisaminoethylether | 0.16 |
| N,N-dimethylbisaminoethylether | 95.24 |
| Σ other compounds | 1.07 |

The invention claimed is:

1. A method for separating at least one of N,N,N'-trimethylbisaminoethylether and N,N-dimethylbisaminoethylether from a mixture A comprising N,N,N'-trimethylbisaminoethylether, N,N-dimethylbisaminoethylether and N,N,N',N'-tetramethylbisaminoethylether, wherein said method comprises the steps of:
   (a) contacting said mixture A with an acylating agent, to form a mixture B comprising N,N,N',N'-tetramethylbisaminoethylether and the amides of N,N,N'-trimethylbisaminoethylether and N,N-dimethylbisaminoethylether;
   (b) at least one of (b1) separating the amide of N,N,N'-trimethylbisaminoethylether from mixture B and (b2) separating the amide of N,N-dimethylbisaminoethylether from said mixture B; and
   (c) at least one of (c1) recovering N,N,N'-trimethylbisaminoethylether from its amide by a transamidation reaction and (c2) recovering N,N-dimethylbisaminoethylether from its amide by a transamidation reaction.

2. The method according to claim 1, further comprising the step (i) of separating N,N,N',N'-tetramethylbisaminoethylether from mixture B.

3. The method according to claim 1, wherein said acylating agent is a $C_{1-6}$-carboxylic acid.

4. The method according to claim 1, wherein step (a) comprises removing water from the mixture.

5. The method according to claim 4, wherein the water removal process is carried out by azeotropic distillation.

6. The method according to claim 1, wherein separation step (b) comprises both steps (b1) and (b2), and wherein step (b2) is performed after step (b1).

7. The method according to claim 1, wherein mixture A further comprises N,N'-dimethylbisaminoethylether, and mixture B comprises the amide of N,N'-dimethylbisaminoethylether.

8. The method according to claim 7, further comprising the step (b3) of separating the amide of N,N'-dimethylbisaminoethylether from mixture B.

9. The method according to claim 1, wherein the separation step is carried out by distillation.

10. The method according to claim 1, wherein the transamidation reaction is performed in the presence of monoethanolamine.

11. The method according to claim 3, wherein the acylating agent is formic acid.

12. The method according to claim 4, wherein step (a) comprises continuously removing water from the mixture.

13. A method for separating at least one of N,N,N'-trimethylbisaminoethylether and N,N-dimethylbisaminoethylether from a mixture A comprising N,N,N'-trimethylbisaminoethylether, N,N-dimethylbisaminoethylether and N,N,N',N'-tetramethylbisaminoethylether, wherein said method comprises the steps of:
 (a) contacting said mixture A with an acylating agent, to form a mixture B comprising N,N,N',N'-tetramethylbisaminoethylether and the amides of N,N,N'-trimethylbisaminoethylether and N,N-dimethylbisaminoethylether;
 (b) either (b1) separating the amide of N,N,N'-trimethylbisaminoethylether from mixture B and then separating the amide of N,N-dimethylbisaminoethylether from said mixture B; or (b2) separating the amide of N,N-dimethylbisaminoethylether from mixture B; and
 (c) at least one of (c1) recovering N,N,N'-trimethylbisaminoethylether from its amide by a transamidation reaction and (c2) recovering N,N-dimethylbisaminoethylether from its amide by a transamidation reaction.

* * * * *